United States Patent
Worthen et al.

(10) Patent No.: US 6,582,398 B1
(45) Date of Patent: *Jun. 24, 2003

(54) METHOD OF MANAGING PATIENT TEMPERATURE WITH A HEAT EXCHANGE CATHETER

(75) Inventors: William J. Worthen, Coto de Caza, CA (US); Scott M. Evans, Santa Ana, CA (US)

(73) Assignee: Alsius Corporation, Irvine, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 09/668,424

(22) Filed: Sep. 22, 2000

Related U.S. Application Data

(63) Continuation-in-part of application No. 09/305,613, filed on May 5, 1999, now Pat. No. 6,368,304, which is a continuation-in-part of application No. 09/253,109, filed on Feb. 19, 1999, now abandoned.

(51) Int. Cl.$^7$ .................................................. A61F 7/12
(52) U.S. Cl. ........................ 604/113; 606/23; 607/96; 607/102
(58) Field of Search ........................... 604/113, 101.05, 604/523; 606/21–26, 194; 607/96, 102, 104–107

(56) References Cited

U.S. PATENT DOCUMENTS

| | | |
|---|---|---|
| 2,308,484 A | 1/1943 | Auzin et al. |
| 3,125,096 A | 3/1964 | Antiles et al. |
| 3,142,158 A | 7/1964 | Podolsky |
| 3,238,944 A | 3/1966 | Hirschhorn |
| 3,282,267 A | 11/1966 | Eidus |
| 3,327,713 A | 6/1967 | Eidus |
| 3,425,419 A | 2/1969 | Dato ............................. 128/400 |
| 3,504,674 A | 4/1970 | Swenson et al. |

(List continued on next page.)

FOREIGN PATENT DOCUMENTS

| | | |
|---|---|---|
| JP | 63-283638 | 11/1988 |
| WO | WO 98/31312 | 4/1998 |
| WO | WO98/26831 | 6/1998 |

OTHER PUBLICATIONS

U.S. patent application Ser. No. 09/305,613, Aliberto et al., App Pending.
U.S. patent application Ser. No. 09/456,110, Luo et al., App Pending.
U.S. patent application Ser. No. 09/477,490, Laserohn et al., App Pending.
U.S. patent application Ser. No. 09/565,039, Worthen et al., App Pending.
U.S. patent application Ser. No. 09/697,667, Noda et al., App Pending.
U.S. patent application Ser. No. 09/668,424, Worthen et al., App Pending.
Jenkins et al., Postbypass Hypothermia and its Relationship to the Energy Balance of Cardiopulmonary Bypass, Journal of Cardiothoracic and Vascular Anesthesia, Apr. 1991, vol. 5, No. 2, pp. 135–138.
Kaye et al., Improving outcome from cardiac arrest in the hospital with a reorganized and strengthened chain of survival: an American view, Resuscitation, 1996, 31, pp. 181–186.
Saadjian et al., Cardiac Output Measurement by Thermodilution, Med. Progr. Technol., 1976, 3, pp. 161–167.
Teoh et al., Accelerated myocardial metabolic recovery with terminal warm blood cardioplegia, J. Thorac. Cardiovasc. Surg., 1986, 91:888–895.

Primary Examiner—Brian L. Casler
Assistant Examiner—Jeremy Thissell
(74) Attorney, Agent, or Firm—Burns, Doane, Swecker & Mathis, L.L.P.

(57) ABSTRACT

A central venous catheter includes coolant supply and return lumens which communicate coolant to and from first and second heat exchange membranes arranged along the distal segment of the catheter. The coolant in the heat exchange membranes removes heat from the patient. Additional lumens are provided for conventional central venous catheter uses.

6 Claims, 2 Drawing Sheets

U.S. PATENT DOCUMENTS

| | | |
|---|---|---|
| 3,738,372 A | 6/1973 | Shioshvili |
| 3,776,241 A | 12/1973 | Magilton |
| 3,897,790 A | 8/1975 | Magilton et al. |
| 3,913,581 A | 10/1975 | Ritson et al. |
| 4,010,795 A | 3/1977 | Stenberg ............... 165/46 |
| 4,111,209 A | 9/1978 | Wolvek et al. ............ 128/400 |
| 4,154,245 A | 5/1979 | Daily |
| 4,249,923 A | 2/1981 | Walda |
| 4,298,006 A | 11/1981 | Parks |
| 4,305,388 A | 12/1981 | Brisson |
| 4,416,280 A | 11/1983 | Carpenter et al. |
| 4,416,281 A | 11/1983 | Cooper et al. ............ 128/400 |
| 4,497,324 A | 2/1985 | Sullivan et al. ............ 128/736 |
| 4,546,759 A | 10/1985 | Solar ........................ 128/1 D |
| 4,583,969 A | 4/1986 | Mortensen |
| 4,632,125 A | 12/1986 | Webler et al. |
| 4,662,383 A | 5/1987 | Sogawa et al. ............ 128/784 |
| 4,672,962 A | 6/1987 | Hershenson |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,754,752 A | 7/1988 | Ginsburg et al. |
| 4,759,349 A | 7/1988 | Betz et al. |
| 4,791,930 A | 12/1988 | Suzuki et al. |
| 4,796,640 A | 1/1989 | Webler ..................... 128/736 |
| 4,813,210 A | 3/1989 | Masuda et al. |
| 4,819,655 A | 4/1989 | Webler ..................... 128/713 |
| 4,823,076 A | 4/1989 | Haines et al. |
| 4,841,981 A | 6/1989 | Tanabe et al. |
| RE32,983 E | 7/1989 | Levy |
| 4,844,074 A | 7/1989 | Kurucz |
| 4,850,958 A | 7/1989 | Berry et al. |
| 4,860,744 A | 8/1989 | Johnson et al. |
| 4,883,455 A | 11/1989 | Leonard |
| 4,899,741 A | 2/1990 | Bentley et al. |
| 4,901,734 A | 2/1990 | Griffin et al. ............... 128/692 |
| 4,920,963 A | 5/1990 | Brader |
| 4,941,475 A | 7/1990 | Williams et al. |
| 4,987,896 A | 1/1991 | Nakamatsu |
| RE33,561 E | 3/1991 | Levy |
| 5,004,456 A | 4/1991 | Botterbusch et al. ......... 604/53 |
| 5,019,075 A | 5/1991 | Spears et al. |
| 5,021,045 A | 6/1991 | Buckberg et al. |
| 5,041,089 A | 8/1991 | Mueller et al. |
| 5,066,578 A | 11/1991 | Wikman-Coffelt |
| 5,078,713 A | 1/1992 | Varney |
| 5,092,841 A | 3/1992 | Spears |
| 5,098,376 A | 3/1992 | Berry et al. |
| 5,106,360 A | 4/1992 | Ishiwara et al. |
| 5,135,474 A | 8/1992 | Swan et al. .................... 604/8 |
| 5,139,496 A | 8/1992 | Hed |
| 5,147,355 A | 9/1992 | Friedman et al. |
| 5,147,385 A | 9/1992 | Beck et al. |
| 5,151,100 A | 9/1992 | Abele et al. |
| 5,158,534 A | 10/1992 | Berry et al. |
| 5,174,285 A | 12/1992 | Fontenot |
| 5,182,317 A | 1/1993 | Winters et al. |
| 5,191,883 A | 3/1993 | Lennox et al. |
| 5,196,024 A | 3/1993 | Barath |
| 5,211,631 A | 5/1993 | Sheaff |
| 5,221,270 A | 6/1993 | Parker ........................ 604/282 |
| 5,230,862 A | 7/1993 | Berry et al. |
| 5,248,312 A | 9/1993 | Langberg |
| 5,250,070 A | 10/1993 | Parodi |
| 5,257,977 A | 11/1993 | Eshel |
| 5,259,839 A | 11/1993 | Burns ........................ 604/99 |
| 5,261,399 A | 11/1993 | Klatz et al. |
| 5,261,411 A | 11/1993 | Hughes |
| 5,262,451 A | 11/1993 | Winters et al. |
| 5,269,758 A | 12/1993 | Taheri |
| 5,271,410 A | 12/1993 | Wolzinger et al. .......... 128/692 |
| 5,275,595 A | 1/1994 | Dobak, III |
| 5,279,598 A | 1/1994 | Sheaff |
| 5,281,213 A | 1/1994 | Milder et al. |
| 5,281,215 A | 1/1994 | Milder |
| 5,324,260 A | 6/1994 | O'Neill et al. |
| 5,324,286 A | 6/1994 | Fowle |
| 5,338,770 A | 8/1994 | Winters et al. |
| 5,342,301 A | 8/1994 | Saab |
| 5,342,693 A | 8/1994 | Winters et al. |
| 5,354,277 A | 10/1994 | Guzman et al. |
| 5,370,616 A | 12/1994 | Keith et al. ................. 604/102 |
| 5,382,234 A | 1/1995 | Cornelius et al. ............ 604/96 |
| 5,411,477 A | 5/1995 | Saab |
| 5,423,807 A | 6/1995 | Milder |
| 5,437,637 A | 8/1995 | Lieber et al. ................ 604/96 |
| 5,437,673 A | 8/1995 | Baust et al. |
| 5,452,582 A | 9/1995 | Longsworth |
| 5,478,309 A | 12/1995 | Sweezer et al. |
| 5,486,204 A | 1/1996 | Clifton ........................ 607/96 |
| 5,486,208 A | 1/1996 | Ginsburg |
| 5,531,776 A | 7/1996 | Ward et al. ................. 607/105 |
| 5,545,134 A | 8/1996 | Hilaire et al. ................ 604/96 |
| 5,545,137 A | 8/1996 | Rudie et al. ................. 604/96 |
| 5,545,161 A | 8/1996 | Imran |
| 5,549,552 A | 8/1996 | Peters et al. ................. 604/96 |
| RE35,352 E | 10/1996 | Peters |
| 5,562,606 A | 10/1996 | Huybregts |
| 5,595,181 A | 1/1997 | Hubbard |
| 5,596,995 A | 1/1997 | Sherman et al. ............ 128/736 |
| 5,609,620 A | 3/1997 | Daily |
| 5,624,392 A | 4/1997 | Saab |
| 5,634,720 A | 6/1997 | Gallup et al. |
| 5,655,548 A | 8/1997 | Nelson et al. |
| 5,656,420 A | 8/1997 | Chien |
| 5,693,080 A | 12/1997 | Wallstén et al. |
| 5,702,435 A | 12/1997 | Maytal |
| 5,733,319 A | 3/1998 | Neilson et al. |
| 5,735,809 A | 4/1998 | Gorsuch |
| 5,755,756 A | 5/1998 | Freedman, Jr. et al. ..... 607/110 |
| 5,758,505 A | 6/1998 | Dobak, III et al. |
| 5,759,182 A | 6/1998 | Varney et al. |
| 5,776,176 A | 7/1998 | Rudie ......................... 607/101 |
| 5,787,715 A | 8/1998 | Dobak, III et al. |
| 5,800,375 A | 9/1998 | Sweezer et al. |
| 5,800,486 A | 9/1998 | Thome et al. ............... 607/105 |
| 5,800,493 A | 9/1998 | Stevens et al. .............. 607/113 |
| 5,833,624 A | 11/1998 | Rom et al. |
| 5,833,688 A | 11/1998 | Sieben et al. ................. 606/41 |
| 5,837,003 A | 11/1998 | Ginsburg ..................... 607/106 |
| 5,861,021 A | 1/1999 | Thome et al. ............... 607/101 |
| 5,868,735 A | 2/1999 | Lafontaine ................... 606/21 |
| 5,879,329 A | 3/1999 | Ginsburg ..................... 604/93 |
| 5,879,347 A | 3/1999 | Saadat .......................... 606/28 |
| 5,902,268 A | 5/1999 | Saab ............................ 604/96 |
| 5,902,299 A | 5/1999 | Jayaraman .................. 606/20 |
| 5,906,588 A | 5/1999 | Safar et al. .................... 604/64 |
| 5,975,081 A | 11/1999 | Hood et al. |
| 5,989,238 A | 11/1999 | Ginsburg ..................... 604/500 |
| 6,042,559 A | 3/2000 | Dobak, III ..................... 604/7 |
| 6,096,068 A | 8/2000 | Dobak, III et al. .......... 607/105 |
| 6,110,168 A | 8/2000 | Ginsburg ..................... 606/27 |
| 6,146,411 A * | 11/2000 | Noda et al. .................. 607/105 |
| 6,149,670 A | 11/2000 | Worthen et al. |
| 6,287,326 B1 * | 9/2001 | Pecor ........................... 604/113 |
| 6,336,911 B1 * | 1/2002 | Westerbeck .................. 422/44 |

\* cited by examiner

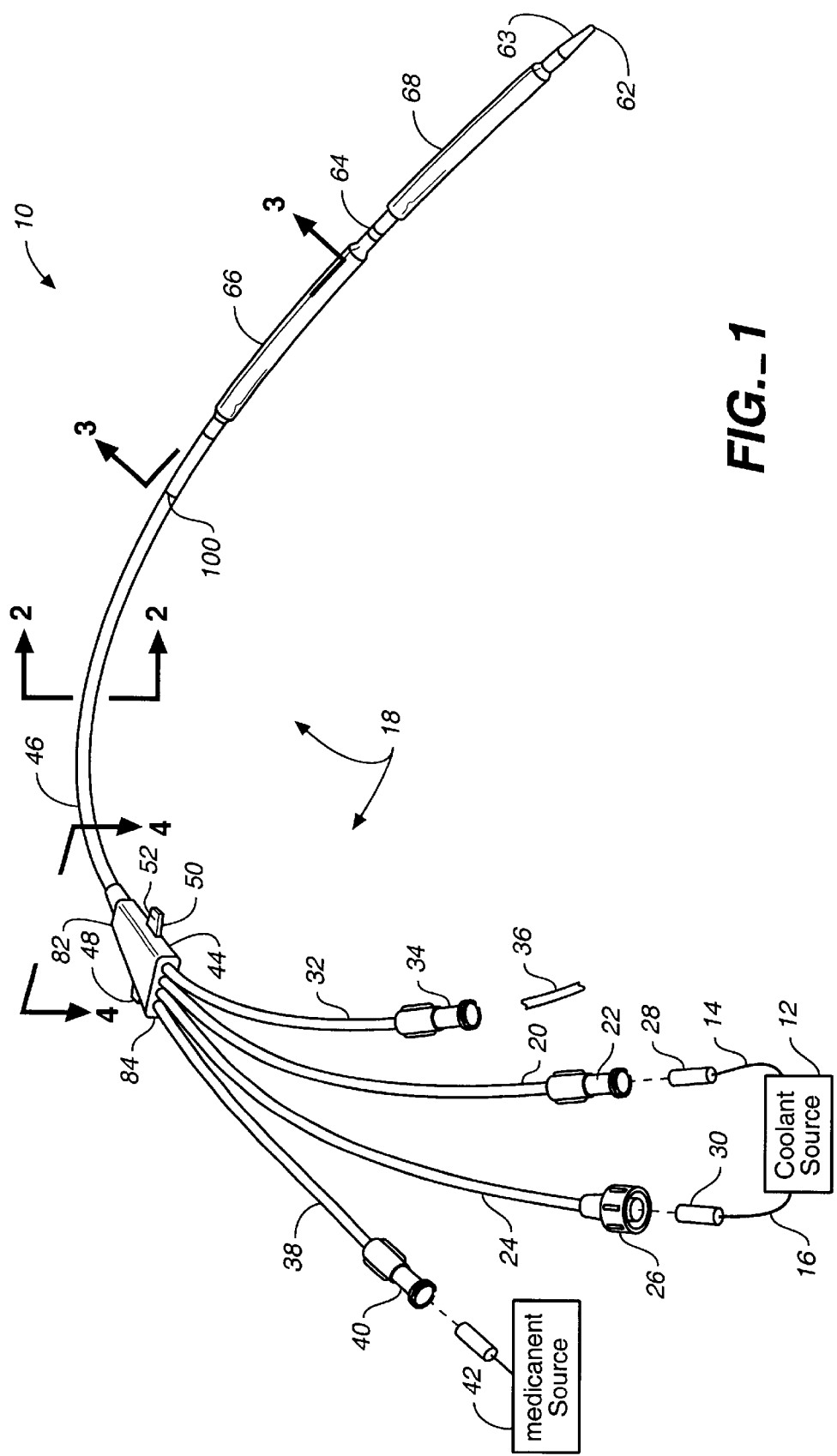
FIG._1

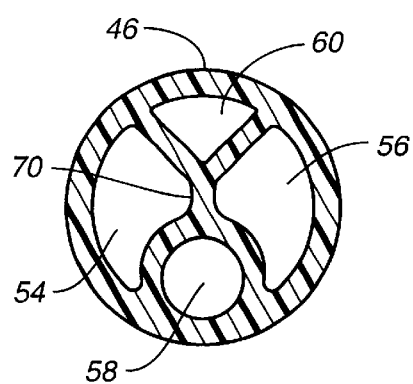
FIG._2
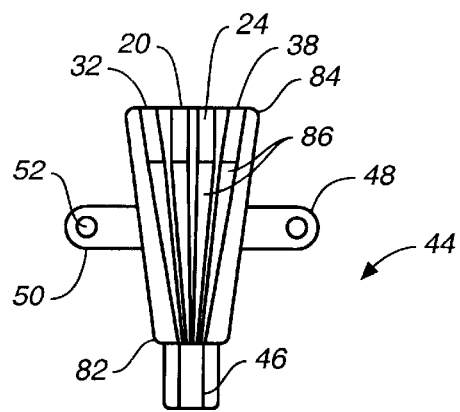
FIG._4
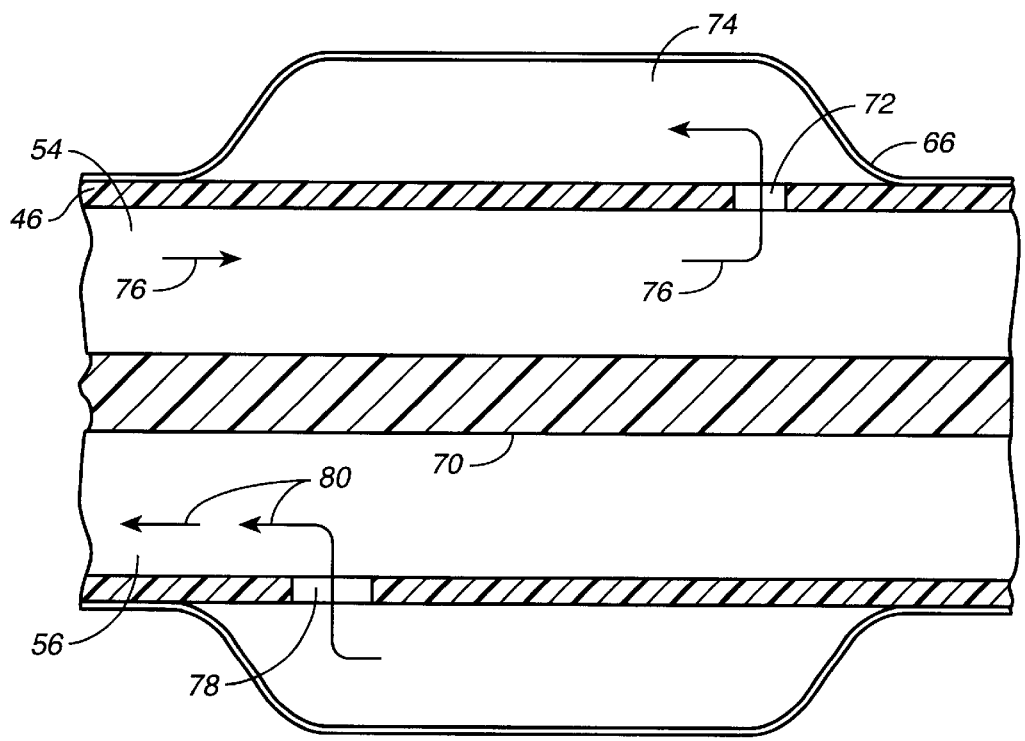
FIG._3

METHOD OF MANAGING PATIENT TEMPERATURE WITH A HEAT EXCHANGE CATHETER

This application is a continuation-in-part of U.S. patent application Ser. No. 09/305,613, filed May 5, 1999, now U.S. Pat. No. 6,368,304 which is a continuation-in-part and claims priority to U.S. patent application No. 09/253,109, filed Feb. 19, 1999 now abandoned.

A method in accordance with an aspect of this invention includes diagnosing a patient as having a myocardial infarction (MI) and cooling the patient below the normal body temperature. This may be accomplished by advancing a cooling catheter into a patient, circulating coolant through the cooling catheter, and measuring the coolant temperature at a first location and at a second location.

FIELD OF THE INVENTION

The present invention relates generally to methods and apparatus for cooling patients for therapeutic purposes, and more particularly to systems for establishing central venous access while providing a means for cooling a patient.

BACKGROUND

It has been discovered that the medical outcome for a patient suffering from severe brain trauma or from ischemia caused by stroke or heart attack is degraded if the patient's body temperature rises above normal (38° C.). It is further believed that the medical outcome for many such patients might be significantly improved if the patients were to be cooled relatively quickly for a short period, e.g., 24–72 hours. Apart from the therapeutic benefits of hypothermia, the outcomes for brain trauma or ischemia patients that develop fevers is worse than for patients that do not develop fevers. Consequently, temperature management for such patients is important, even when hypothermia is not to be used to treat the patients. Moreover, prophylactic short-term hypothermia might help patients undergoing minimally invasive heart surgery and aneurysm surgery.

The affected organ, in any case, is the brain. Accordingly, systems and methods have been disclosed that propose cooling blood flowing to the brain through the carotid artery. An example of such systems and methods is disclosed in co-pending U.S. patent application Ser. No. 09/063,984, filed Apr. 21, 1998, owned by the present assignee and incorporated herein by reference. In the referenced application, various catheters are disclosed which can be advanced into a patient's carotid artery and through which coolant can be pumped in a closed circuit, to remove heat from the blood in the carotid artery and thereby cool the brain. The referenced devices have the advantage over other methods of cooling (e.g., wrapping patients in cold blankets) of being controllable, relatively easy to use, and of being capable of rapidly cooling and maintaining blood temperature at a desired set point.

As recognized in co-pending U.S. patent application Ser. No. 09/133,813, filed Aug. 13, 1998, owned by the present assignee and incorporated herein by reference, the above-mentioned advantages in treating brain trauma/ischemic patients by cooling can also be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system.

Moreover, since many patients already are intubated with central venous catheters for other clinically approved purposes anyway, providing a central venous catheter that can also cool the blood, if only to manage temperature and thereby ameliorate fever spikes, requires no additional surgical procedures for those patients. A cooling central venous catheter is disclosed in the present assignee's co-pending U.S. patent application Ser. No. 09/253,109, filed Feb. 19, 1999 and incorporated herein by reference. The present invention is directed to such a device.

SUMMARY OF THE INVENTION

A heat exchange catheter, preferably made of urethane, includes a catheter body defining at least a coolant supply lumen and a coolant return lumen. First and second heat exchange membranes are disposed along a distal portion of the catheter body, and the heat exchange membranes communicate with one or more of the lumens. With this structure, coolant can be supplied to the heat exchange membranes via the coolant supply lumen and received from the heat exchange membranes via the coolant return lumen to effect a closed loop heat exchanger for cooling and/or warming a patient.

Preferably, the first and second heat exchange membranes define first and second interiors respectively communicating with first and second coolant supply ports in the coolant supply lumen. Also, first and second coolant return ports are formed in the coolant return lumen, and coolant flows from the heat exchange membranes through the return ports. At least one anchor can be engaged with the catheter body to fasten the catheter to a patient.

In addition to the coolant supply and return lumens, the catheter can define a drug delivery lumen and a guide wire lumen. A connector manifold can be engaged with the catheter body to interconnect the lumens with respective connector lines. More specifically, the connector manifold defines plural channels, and each channel establishes a respective pathway for fluid communication between a respective connector line and a respective lumen. As set forth in detail below, the anchor is on the connector manifold.

To provide for infusing medicament into a patient while simultaneously cooling the patient, at least one drug delivery port is formed in the catheter body. Preferably, the drug delivery port is formed at a location that is between two adjacent heat exchange membranes to establish a pathway for fluid communication from the drug delivery lumen to a location outside the catheter body. If desired, additional drug delivery ports can be formed along the length of the catheter.

In another aspect, a method for making a heat exchange catheter includes disposing a multi-lumen catheter body in a connector manifold mold, and disposing plural connector tubes in the connector manifold mold. Also, the method includes interconnecting a respective lumen with a respective connector tube using a mandrel, and then directing a plastic material into the connector manifold mold. The mandrels are then removed, such that a respective channel is defined between each respective lumen and its connector line.

In another aspect, a method is disclosed for treating a patient. The method includes advancing a heat exchange catheter device into the patient, and then circulating coolant through the catheter device while preventing infusion of the coolant directly into the patient's bloodstream. Per the present invention, the catheter device includes a heat exchange region that is established by: one or more heat exchange membranes, or one or more hollow fibers, or one or more chamber-defining enclosures.

In still another aspect, a catheter configured as a Swan-Ganz catheter or central venous catheter has at least one balloon-like membrane distally located on the catheter for heating or cooling blood in a patient. More particularly, the membrane defines an interior communicating with a coolant supply lumen of the catheter and with a coolant return lumen of the catheter, to circulate coolant through the interior of the membrane.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a perspective view of the present cooling catheter, schematically showing a medicament source and coolant source in an exploded relationship with the catheter;

FIG. 2 is a cross-sectional view as seen along the line 2—2 in FIG. 1;

FIG. 3 is a cross-sectional view as seen along the line 3—3 in FIG. 1; and

FIG. 4 is a top view of the interior of the connector manifold, as seen along the line 4—4 in FIG. 1.

DETAILED DESCRIPTION OF THE PREFERRED EMBODIMENT

Referring initially to FIG. 1, a therapeutic catheter system, generally designated 10, is shown for establishing and maintaining hypothermia in a patient, or for attenuating a fever spike in a patient and then maintaining normal body temperature in the patient. Commencing the description of the system 10 at the proximal end, as shown the system 10 includes a cooling source 12 that can be a water-bath system or a TEC-based system such as either of the systems disclosed in co-pending U.S. patent application Ser. No. 09/220,897, filed Dec. 24, 1998 and incorporated herein by reference, or U.S. patent application Ser. No. 09/260,950, filed Mar. 2, 1999, also incorporated herein by reference. In any case, the coolant source provides coolant such as saline through a coolant supply line 14, and coolant is returned to the source 12 via a coolant return line 16. A catheter, generally designated 18, includes a source tube 20 terminating in a fitting such as a female luer fitting 22. Also, the catheter 18 has a return tube 24 terminating in a fitting such a male luer fitting 26. The fittings 22, 26 can be selectively engaged with complementary fittings 28, 30 of the lines 14, 16 to establish a closed circuit coolant path between the catheter 18 and coolant source 12.

Additionally, the catheter 18 includes a guide wire and primary infusion tube 32 that terminates in a fitting such as a female luer 34. A guide wire 36 can be advanced through the tube 32 in accordance with central venous catheter placement principles, or medicament or other fluid can be infused through the guide wire and primary infusion tube 32. Moreover, a secondary infusion tube 38 with female luer fitting 40 can be selectively engaged with a medicament source 42 for infusing fluid from the source 42 through the secondary tube 38.

As discussed further below, the tubes 20, 24, 32, 38 are held in a distally-tapered connector manifold 44. As also set forth further below, the connector manifold 44 establishes respective pathways for fluid communication between the tubes 20, 24, 32, 38 and respective lumens in a catheter body 46.

A suture anchor 48 advantageously is formed on the connector manifold 44 for suturing the catheter 18 to a patient in accordance with central venous catheter operating principles. In one intended environment, the suture anchor 48 includes opposed ears 50 formed with respective suture holes 52. Other equivalent anchor structure can be used to hold the catheter 18 onto the patient, however, including surgical tape. When the catheter is a so-called Swlan-Ganz catheter, i.e., a catheter of the type disclosed in U.S. Pat. No. 3,995,623, incorporated herein by reference, the anchor 48 typically would not be provided.

In cross-reference to FIGS. 1 and 2, the catheter body 46 includes at least two lumens, and in the preferred embodiment the catheter body 46 includes at least four lumens. More specifically, the catheter body 46 defines a generally wedge-or triangular-shaped (in the transverse cross-section shown) coolant supply lumen 54, a generally wedge-shaped coolant return lumen 56, a round guide wire lumen 58, and a wedge-shaped secondary infusion lumen 60. As mentioned above, however, the catheter can be a Swan-Ganz catheter, in which case additional lumens can be provided for Swan-Ganz catheter applications, including a lumen for inflating an anchoring balloon for holding the distal tip of the catheter in an appropriate blood vessel for various heart-related measurements and another lumen for holding a wire or wires that are attached to one or more distally-located sensors, such as temperature sensors, pressure sensors, gas sensors, and electrical sensors.

In any case, the connector manifold 44 establishes a pathway for fluid communication between the coolant supply tube 20 and the coolant supply lumen 54. Likewise, the connector manifold 44 establishes a pathway for fluid communication between the coolant return tube 24 and the coolant return lumen 56. Further, the connector manifold 44 establishes a pathway for fluid communication between the guide wire and primary infusion tube 32, and the guide wire lumen 58, which terminates at an open distal hole 62 defined by a distally tapered and chamfered distal tip 63 of the catheter body 46. Also, the connector manifold 44 establishes a pathway for fluid communication between the secondary infusion tube 38 and the secondary infusion lumen 60, which terminates at an infusion port 64 in a distal segment of the catheter body 46. Additional ports can be provided for each lumen 58, 60 along the length of the catheter.

Referring now to FIGS. 1 and 3, at least proximal and distal thin-walled heat exchange membranes 66, 68 are arranged along the last fifteen or so centimeters of the catheter body 46 and are bonded to the outer surface of the catheter body 46, with the infusion port 64 being located between the heat exchange membranes 66, 68. Thus, each heat exchange membrane is about six centimeters to seven and one-half centimeters in length, with the heat exchange membranes being longitudinally spaced from each other along the catheter body 46 in the preferred embodiment shown. Essentially, the heat exchange membranes 66, 68 extend along most or all of that portion of the catheter 46 that is intubated within the patient. The heat exchange membranes can be established by a medical balloon material.

The heat exchange membranes 66, 68 can be inflated with coolant from the coolant source 12 as supplied from the coolant supply lumen 54, and coolant from the heat exchange membranes 66, 68 is returned via the coolant return lumen 56 to the coolant source 12. In their inflated configurations, the heat exchange membranes define a diameter of about ten French, and preferably no more than twelve French. Thus, the heat exchange membranes 66, 68 are relatively long and comparatively thin, to advantageously avoid excessively blocking blood flow through the vena cava while nevertheless effecting patient cooling.

As shown in FIG. 3, a wall 70 separates the coolant supply and return lumens 54, 56. Taking the proximal heat exchange membrane 66 as an example, a supply port 72 is formed in the catheter body 46 through which coolant from the supply lumen 54 can flow into the interior 74 of the heat exchange membrane 66, as indicated by the arrows 76. Moreover, a return port 78 is formed in the catheter body 46, and coolant can flow out of the heat exchange membrane 66 through the return port 78 and into the return lumen 56, as indicated by the arrows 80. As can be appreciated in reference to FIG. 3, for each heat exchange membrane 66, 68, the respective coolant supply port is distal to the respective coolant return port, to optimize fluid flow and heat transfer, although if desired the direction of fluid flow can be in the opposite direction. Both the coolant supply and coolant return lumens 54, 56 terminate proximal to the distal tip 63. For example, the coolant return lumen 56 can terminate just distal of the coolant return port for the distal heat exchange membrane 68, and the coolant supply lumen can terminate just distal of the coolant supply port of the distal heat exchange membrane 68.

In any case, it may now be appreciated that coolant is circulated through the catheter device 18 in a closed loop. That is, infusion of the coolant directly into the patient's bloodstream is prevented. As detailed above, the catheter device includes a heat exchange region established by one or more heat exchange membranes. Alternatively, the heat exchange region can be established by or one or more hollow fibers, or one or more chamber-defining enclosures, such as metal or plastic bellows-type enclosures.

In the preferred embodiment, the components of the catheter 18 are made of urethane, and more preferably are made of an aromatic, polyether-based polyurethane, although other suitable materials can be used. In a specific embodiment, the tubes 20, 24, 32, 38 are made of Tecothane TT-1095A made by Thermedics, Inc. of Woburn, Mass. Also, the heat exchange membranes 66, 68 are made of Pellethane 2363-65D, made by Dow Chemical Corp. In contrast, the catheter body 46 is made of Tecothane TT-2055D-B20 with Barium Sulfate radiopacifying agent incorporated into the polymer matrix for optimum visualizing during fluoroscopic maneuvering to a desired location. The catheter 18 can be coated with an anti-microbial agent and an anti-clotting agent if desired.

Now referring to FIG. 4, the details of the connector manifold 44 can be seen. As shown, the preferred connector manifold 44 is flat and wedge-shaped, with the distal end 82 of the connector manifold 44 being narrower than the proximal end 84. Within the connector manifold 44, plural channels 86 are established. As can be appreciated in reference to FIG. 4, each channel 86 establishes a respective pathway for fluid communication between a respective connector line 20, 24, 32, 38 and a respective lumen 54, 56, 58, 60. Owing to the wedge shape of the connector manifold 44, the tubes 20, 24, 32, 38 are closely juxtaposed to each other near the distal end 82 of the connector manifold 44.

In making the connector manifold 44, the tubes 20, 24, 32, 38 are positioned on what will become the interior of the connector manifold, and the catheter body 46 likewise is positioned on the connector manifold, closely spaced from the distal ends of the tubes. A respective mandrel is then advanced into each tube and the lumen of the catheter body 46 that is to communicate with the tube. Next, plastic is directed over and around the tubes, mandrels, and catheter body 46 by insert molding. The mandrels are removed after the plastic hardens, establishing the channels 86.

As envisioned by the present invention, the structure set forth above can be used in many medical applications to cool a patient and/or to maintain temperature in a normothermic or hypothermic patient, for purposes of improving the medical outcomes of patients on whom, e.g., aneurysm surgery is to be performed, preferably while the patient's temperature is below normal body temperature. The structure can then be used to rewarm the patient in a controlled manner by circulating warm coolant through the structure, or by otherwise regulating natural body re-warming by circulating coolant that is maintained at an appropriate cool (relative to normal body temperature) or warm (relative to normal body temperature) temperature through the structure.

As another example, head trauma can be treated by and after lowering and maintaining the patient's temperature below normal body temperature. Or, cardiac arrest can be treated while the patient's temperature is below normal body temperature. Yet again, minimally invasive heart surgery can be performed on the patient while the patient's temperature is below normal body temperature. And, cardiac arrest in the patient can be treated by and while the patient's temperature is below normal body temperature. Also, the present invention understands that for certain patients, e.g., stroke victims, it is important to maintain the temperature of a patient at or below normal body temperature, when the patient runs or attempts to run a fever. For severe . ischemic stroke victims, the malady can be treated by maintaining the patient's body temperature at a hypothermic level.

If desired, a temperature sensor 100 such as a thermistor or other suitable device can be attached to the catheter 18 as shown. The sensor 100 can be mounted on the catheter 18 by solvent bonding at a point that is proximal to the membranes 66, 68. Or, the sensor 100 can be disposed in a lumen of the catheter 18, or attached to a wire that is disposed in a lumen of the catheter 18, with the sensor hanging outside the catheter 18. Alternatively, a separate temperature probe can be used, such as the esophageal probe disclosed in co-pending U.S. patent application Ser. No. 09/282,971, filed Mar. 31, 1999 and incorporated herein by reference. As yet another alternative, a rectal probe or tympanic temperature sensor can be used. In any case, the sensor is electrically connected to the coolant source 12 for control of the temperature of the coolant as described in the above-referenced '897 and '940 applications.

A method in accordance with the present includes the step of disposing a patient in an operating room of a medical facility, the step of advancing a cooling catheter into the patient where the cooling catheter housing an internally circulating coolant having a coolant temperature, and the step of regulating the coolant temperature to cool the patient.

The step of regulating the coolant temperature includes measuring the coolant temperature at a first location and a second location, calculating the temperature difference between the two inventions, and using the temperature difference between the two locations, to determine the amount of heat lost by the patient and to determine the rate of heat loss by the patient. Preferably, the first location and the second location are located near the proximal end of the catheter body to measure coolant temperature in the coolant supply lumen and coolant return lumen, respectively. It can be appreciated, however, that measuring the coolant temperature can be accomplished at virtually any two locations in the catheter body to result in useful data.

Determining the heat lost by the patient (the amount of patient cooling) is accomplished by calculating the heat gained by the coolant during a period and correlating the relationship between the coolant heat gained and the patient heat lost. Once the relationship between coolant heat transfer and patient heat transfer is correlated, the amount that the patient has been cooled by the cooling catheter can be found.

Determining the rate of heat lost by the patient is useful for many reasons. One reason is that when a target patient cooling rate is established and when the actual rate of heat lost by a patient is measured, then, this target cooling rate can be compared to an actual patient cooling rate. This assures that a patient will not cool beyond acceptable levels.

According to one aspect of the invention, the patient is cooled for surgery, is re-warmed after a surgery with a target re-warm rate being established. An inactive cooling catheter is advanced into the patient. In an inactive cooling catheter, there is no circulation of cooling fluid, or the circulating cooling fluid has a temperature that is ineffectual. The patient warms at an actual re-warm rate. The actual re-warm rate is measured and compared to the target re-warm rate. If the actual re-warm rate exceeds the target re-warm rate, then the cooling catheter is selectively activated.

Selectively activating the cooling catheter reduces the actual re-warm rate, optimally preventing the target re-warming from being exceeded. Activating the cooling catheter to reduce the re-warm rate of the patient when the patient re-warm rate exceeds a target rate prevents a hyper thermic patient condition.

It can be appreciated that the step of activating the cooling catheter can alternatively be performed as the re-warm rate increases and approaches the target re-warm rate.

A further method in accordance with an aspect of this invention includes the step of disposing a vital patient in a recovery room of a hospital, e.g. an intensive care unit. This aspect of the invention relies on monitoring the patient's vital signs, including temperature, and advancing a cooling catheter into the patient to manage a patient temperature by regulating the coolant temperature.

The methods described can include an operating room patient and employ the step of disposing the patient in an operating room of a medical facility. Accordingly, the present invention is useful during various surgical procedures. While the particular CENTRAL VENOUS CATHETER WITH HEAT EXCHANGE MEMBRANE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

What is claimed is:

1. A method for managing patient temperature, comprising:

disposing a patient in a room of a medical facility, cooling a patient to prepare the patient for cardiovascular bypass surgery;

performing a cardiovascular bypass surgery on the patient;

re-warming a patient after the cardiovascular bypass surgery is performed;

advancing a cooling catheter into the patient, the cooling catheter housing an internally circulating coolant having a coolant temperature; and regulating the coolant temperature to assure that the step of re-warming a patient does not result in hyperthermic patient condition.

2. A method as set forth in claim 1, wherein the step of regulating the coolant temperature includes measuring the coolant temperature at a first location and at a second location and establishing a temperature difference between the first location and the second location.

3. A method as set forth in claim 1, wherein the step of regulating the coolant temperature includes using the temperature difference between the first location and the second location to determine the amount of heat lost by the patient.

4. A method as set forth in claim 1, wherein the step of regulating the coolant temperature includes measuring the coolant temperature at a first location and a second location to determine the rate of heat loss by the patient.

5. A method as set forth in claim 1, wherein the step of regulating the coolant temperature includes establishing a target patient re-warm rate.

6. A method as set forth in claim 1, wherein the step of regulating the coolant temperature includes establishing a target patient re-warm rate, the patient has an actual re-warm rate;

measuring the actual re-warm rate; and activating the cooling catheter to reduce the actual re-warm rate of the patient when the measured actual re-warm rate exceeds the target re-warm rate.

* * * * *